United States Patent [19]

Pews

[11] 4,131,619

[45] Dec. 26, 1978

[54] PREPARATION OF 2-CHLORO-4-TOLUENESULFONYL CHLORIDE

[75] Inventor: R. Garth Pews, Midland, Mich.

[73] Assignee: The Dow Chemical Company, Midland, Mich.

[21] Appl. No.: 888,887

[22] Filed: Mar. 22, 1978

[51] Int. Cl.$^2$ .................. C07C 143/28; C07C 143/40
[52] U.S. Cl. ........................... 260/543 R; 260/505 R; 260/505 E
[58] Field of Search ............ 260/543 R, 505 R, 505 E

[56] References Cited

U.S. PATENT DOCUMENTS

| | | | |
|---|---|---|---|
| 3,364,258 | 1/1968 | Jong | 260/543 |
| 3,935,237 | 1/1976 | Davidsohn | 260/505 S |

FOREIGN PATENT DOCUMENTS

| | | |
|---|---|---|
| 956857 | 4/1964 | United Kingdom. |
| 1017976 | 1/1966 | United Kingdom. |

OTHER PUBLICATIONS

Gilbert, Interscience, p. 371 (1965).
Gilbert, Ind. Eng. Chem. vol. 45, pp. 2065–2066 (1953).
Sutter et al., Organic Reactions, vol. III, p. 144 (1946).
Chem. Abst. vol. 59:9748(b) (1963).

*Primary Examiner*—Gerald A. Schwartz
*Attorney, Agent, or Firm*—L. Wayne White; Michael L. Glenn

[57] ABSTRACT

The title compound is prepared in high yield and purity from toluene in a process comprising the steps of:

(a) reacting by contacting toluene with sulfur trioxide in an anhydrous chlorinated hydrocarbon medium, to thereby form a solution of toluenesulfonic acid in the chlorinated hydrocarbon medium;

(b) reacting by contacting chlorine gas with the product from step (a) in the presence of a catalytic amount of iodine, to thereby form a solution of chlorotoluenesulfonic acid in the chlorinated medium; and (c) reacting by contacting chlorosulfonic acid with the product from step (b), to thereby form a solution of chlorotoluenesulfonyl chloride in the chlorinated medium.

As an example, the title compound is obtained in a yield more than 90 percent based on toluene, using 1,2-dichloroethane as the reaction medium.

4 Claims, No Drawings

PREPARATION OF 2-CHLORO-4-TOLUENESULFONYL CHLORIDE

BACKGROUND OF THE INVENTION

This invention relates to the preparation of 2-chloro-4-toluenesulfonyl chloride from toluene in a chlorinated hydrocarbon medium.

Direct chlorination reactions of aromatic compounds are often nonselective in aromatic systems and give a random distribution of chlorinated derivatives. The inadequacies of direct chlorination as a method of producing aryl chlorides have brought about attempts to utilize the more selective substitution patterns of sulfonation reactions. However, known methods for effecting selective chlorination by means of the sulfonation of aromatic compounds have not been implemented commercially because the separate steps of selective sulfonation, nuclear chlorination at other sites, conversion to the sulfonyl chloride, and displacement of the sulfonyl chloride group by a chlorine have required different reaction mediums and conditions to effect each of the desired intermediates in high yield. Each process step, of course, adds considerable expense to the overall process and makes commercialization economically unattractive.

Consequently, direct chlorination, as recited in U.S. Pat. No. 4,045,502, is the conventional commercial process employed by the art to prepare 4-chlorotoluene from toluene, despite the concurrent production of a high proportion of other monochlorotoluene isomers.

The practice of this invention is useful to prepare a basic intermediate for a number of dyes, herbicides and other useful compounds. This invention is particularly useful in the preparation of 2,4-dichlorobenzotrifluoride, a precursor of commercial herbicides as illustrated in British Pat. No. 1,321,563.

SUMMARY OF THE INVENTION

An improved process has now been discovered for the preparation of 2-chloro-4-toluenesulfonyl chloride. This process comprises the steps of:

(a) reacting by contacting toluene with sulfur trioxide in an anhydrous, chlorinated hydrocarbon medium to produce in the medium toluenesulfonic acid consisting essentially of the 4-toluenesulfonic acid isomer;

(b) reacting by contacting the toluenesulfonic acid in the chlorinated hydrocarbon medium from step (a) with gaseous chlorine in the presence of an accelerating amount of an iodine catalyst to produce in the medium chlorotoluenesulfonic acid consisting essentially of the 2-chloro-4-toluene sulfonic acid isomer; and (c) reacting by contacting the chlorotoluenesulfonic acid in the chlorinated hydrocarbon medium from step (b) with chlorosulfonic acid to produce in the medium chlorotoluenesulfonyl chloride consisting essentially of the 2-chloro-4-toluenesulfonyl chloride isomer.

Practice of the present invention leads to the production of 2-chloro-4-toluenesulfonyl chloride from toluene in a single reactor and a single reaction medium without the need for multiple purification and separation steps. 2-Chloro-4-toluenesulfonyl chloride is thus produced in high yield and purity.

DETAILED DESCRIPTION OF THE EMBODIMENTS

The anhydrous, chlorinated hydrocarbon medium to be employed in the practice of this invention can suitably be an aliphatic hydrocarbon having 1 to 4 carbon atoms and 2 to 6 chlorine substituents. The chlorinated hydrocarbon is advantageously not perchlorinated. The chlorinated hydrocarbon can suitably comprise other substituents substantially inert in this process (e.g., fluorine, bromine and the like) but advantageously the chlorinated hydrocarbon possesses only hydrogen and chlorine substituents on the carbon skeleton. An anhydrous, chlorinated hydrocarbon medium consisting essentially of dichloromethane or 1,2-dichloroethane is particularly advantageous in the practice of the method of this invention, with 1,2-dichloroethane being the medium of choice. The term anhydrous as it is used herein means that the medium should contain no more than about 200 parts per million (ppm) by weight of water, preferably no more than about 50 ppm.

The amount of solvent to be used in the medium is determined by, among other factors, the solubility of the toluene and its derivatives present in the various steps in this solvent. Of course, there must be enough solvent present to maintain all of the toluene and its derivatives in solution. However, an excess of solvent is suitable, though a large excess necessitates longer distillation to isolate the chlorotoluenesulfonyl chloride. The method of this invention is particularly applicable to mediums in which the toluene is initially present in a concentration from about 10 to about 40 percent by weight. The method of this invention can be practiced in a batchwise or a continuous process.

Step (a)

The manner in which the reactants are contacted in the anhydrous chlorinated medium in step (a) is not critical to the practice of this invention so long as monosulfonation in the para position is predominantly effected. It is generally advantageous, however, to sparge gaseous sulfur trioxide through the reaction medium containing toluene. More advantageously, the sulfur trioxide is dissolved or diluted with the chlorinated hydrocarbon medium itself at a temperature below about 20° C. and this solution is then added to the main body of the chlorinated hydrocarbon medium in which toluene is present. The sulfur trioxide desirably should not reside in the medium for extended periods or reactions with the chlorinated hydrocarbon in the medium can occur.

Normally, an equimolar amount or slight molar excess of sulfur trioxide is brought together with the toluene. The reaction is relatively rapid and a large excess of sulfur trioxide to effect almost quantitative sulfonation is unnecessary. Furthermore, excess sulfur trioxide can react with the solvent or enter into other untoward reactions. A less than equimolar amount of sulfur trioxide can be employed, but leads to incomplete conversion of toluene.

The reaction is normally conducted by bringing together the reactants at a temperature of from about −10° C. to about 20° C., preferably about 5° C. to about 10° C. Lower temperatures than those in the above preferred ranges are operable, but require excessive and uneconomical cooling of the medium. Higher temperatures than those in the above preferred ranges are also operable, but can accelerate the reaction of sulfur trioxide with the solvent and can cause resinification during the sulfonation.

The atmosphere above the medium is desirably substantially inert to reactants and products at the above conditions. For example, the atmosphere can consist of nitrogen.

Certain additives can be introduced into the anhydrous medium which increase the ratio of para to ortho substitution or reduce the formation of by-products during sulfonation. The use of a small amount, i.e., about 0.5 percent of about 2 percent by weight based on toluene, of ditolylsulfone or diphenylsulfone is desirable to increase the percentage of the para-substituted isomer in the product. The ditolylsulfone is preferred as an orienting agent.

After the sulfonation step is complete, the toluenesulfonic acid product can be nuclear chlorinated and then converted to the corresponding sulfonyl chloride or alternatively, but less desirably, the above steps can be performed in the reverse order. The latter order is less desirable because the conversion to the sulfonyl chloride produces an acid phase which should be removed from contact with the medium prior to the nuclear chlorination step to minimize resinification of the product. Furthermore, the nuclear chlorination of the toluenesulfonyl chloride generally produces a ratio of isomers which is less favorable in the embodiment wherein the product is subsequently photochlorinated.

Step (b)

The manner in which the toluenesulfonic acid and chlorine gas are brought together in the anhydrous medium, is not necessarily critical to the practice of this invention so long as monochlorination is substantially completely effected. The chlorine can conveniently be sparged through the medium with mixing so as to effect substantially complete monochlorination of the toluenesulfonic acid with only an equimolar amount or a slight excess of chlorine. The point at which substantially complete monochlorination is effected can be determined from the hydrogen chloride evolved or analysis of the product. Chlorine gas collects in the atmosphere above the medium when the chlorine is introduced in a manner which effects incomplete reaction or when an excess amount of chlorine is employed. Desirably, this atmosphere consists of gases substantially inert to chlorine and the toluene derivatives in the medium. Conveniently, this atmoshpere is also free of oxygen and other side-chain chlorination promoters, so that the atmosphere containing the excess chlorine can be cycled into a medium containing toluenesulfonic acid to effect nuclear chlorination. However, chlorine in the atmosphere is advantageously not kept in contact with the medium during the conversion to the sulfonyl chloride or more particularly during the sulfonation step.

The gaseous chlorine is brought together with the toluenesulfonic acid in the presence of an amount of iodine which accelerates nuclear chlorination. This amount of iodine is operably in the range from about 0.25 percent to about 5 percent, preferably about 0.5 percent to about 2 percent, of the weight of the toluenesulfonic acid present prior to chlorination. Iodine is preferably introduced into the medium in its molecular form, but salts of iodine such as potassium iodide or sodium iodide are suitable so long as sufficient mixing is employed to keep the catalyst in contact with the reactants. The iodine can be employed as a catalyst in combination with other nuclear chlorination catalysts, such as finely divided iron, but it is desirable to use iodine alone.

The toluenesulfonic acid and the chlorine are brought together at a temperature preferably of from about 50° C. to about 130° C., more preferably about 90° C. to about 110° C. Temperatures both lower and higher than the preferred ranges immediately above are suitable, but at lower temperatures the chlorination is uneconomically slow and at higher temperatures resinification of the toluene derivatives occurs to a greater degree.

Step (c)

The manner in which the chlorotoluenesulfonic acid and the chlorosulfonic acid are brought together is not critical to the practice of this invention, so long as the sulfonic acid is substantially completely converted to the corresponding sulfonyl chloride. The chlorosulfonic acid can suitably be brought together with said sulfonic acid in any convenient manner known to the art at a temperature of from about −20° C. to about 70° C., preferably from about 20° C. to about 60° C. Advantageously, the medium is stirred or otherwise agitated as the reactants are brought together to promote rapid reaction and good heat transfer in the medium. Suitably an equimolar amount of the chlorosulfonic acid is brought together with the chlorotoluenesulfonic acid, but it is more desirable to use an excess amount of chlorosulfonic acid to effect a higher degree of conversion. Preferably, an excess of chlorosulfonic acid of from about 5 to about 20 percent of the molar amount of chlorotoluenesulfonic acid present is employed. If in a single contact only a low degree of conversion of the chlorotoluenesulfonic acid to the sulfonyl chloride derivative is effected, the unconverted chlorotoluenesulfonic acid can be cycled back to this step.

After the conversion to the sulfonyl chloride is substantially complete, the agitation of the medium is terminated. The medium then separates into an acid phase consisting predominantly of sulfuric acid and chlorosulfonic acid and an organic phase consisting essentially of the solvent and the toluenesulfonyl chloride product. The two phases can be separated by any convenient means known to the art. To obtain a higher yield of product, the acid phase is then extracted with fresh anhydrous solvent and this solvent is combined with the separated organic phase. The organic phase can be extracted with water or a dilute acid solution to remove residual amounts of sulfuric acid. The organic phase is desirably separated from the water employed in the extraction and azeotropically distilled to remove residual amounts of water.

The product can be isolated in any manner known to the art. The iodine catalyst is first removed in any manner known to the art, as by aqueous extraction with a suitable agent. Conveniently, the water used to extract residual acid from the organic phase can contain a suitable amount of sulfur dioxide or sodium sulfite or some other agent which will convert the iodine chlorination catalyst to a form readily extracted into the aqueous phase. The product is isolated as a substantially dry powder by continued distillation of the chlorinated hydrocarbon from the medium after the azeotropic distillation is complete.

To illustrate the high yield and purity effected by this process, in the more desirable embodiments of this invention theoretical yields of chlorotoluenesulfonyl chloride isomers of greater than 95 mole percent based on toluene can be effected. Further, normally more than 85 percent of the toluenesulfonyl chloride isomers is the 2-chloro-4-toluenesulfonyl chloride isomer in these more desirable embodiments.

The examples that follow illustrate the invention, but are not to be taken as limiting its scope.

EXAMPLE 1

To a reaction medium of 100 milliliters (ml) of 1,2-dichloroethane containing 1 gram of diphenylsulfone are simultaneously added a solution of 0.5 mole of toluene diluted to 125 ml with 1,2-dichloroethane and a solution of 0.55 mole of sulfur trioxide dissolved in 100 ml of 1,2-dichloroethane. The toluene and sulfur trioxide are brought together slowly and with mixing so as to maintain a temperature in the range from 5° C. to 10° C. during sulfonation. After the addition is complete, a small amount of the medium is removed, the toluenesulfonic acid isomers are quantitatively converted to the corresponding toluene sulfonyl chloride isomers and said sulfonyl chloride isomers analyzed by gas-liquid chromatography to determine the isomer distribution. The weight percent of each isomer is 95.1 percent of p-toluenesulfonyl chloride, 3.6 percent for o-toluenesulfonyl chloride and 1.2 percent for m-toluenesulfonyl chloride.

To the remaining amount of the reaction medium is added 0.5 gram of iodine. The temperature of the medium is elevated to 90° C. and chlorine gas is sparged through the reaction medium to effect chlorination. During chlorination the temperature is maintained in a range from 90° C. to 120° C. Samples of the medium are taken periodically for nuclear magnetic resonance (NMR) analysis. When the NMR analysis indicates an equal number of hydrogen atoms of aromatic and aliphatic character in the toluene derivative, the flow of chlorine gas is stopped.

To the reaction medium maintained at a temperature in the range from 50° C. to 60° C. is added dropwise with stirring 0.55 mole of chlorosulfonic acid. One hour after the addition is complete, the medium is cooled to 20° C. and the acid phase is separated from the organic phase. The acid phase is extracted with 50 ml of fresh 1,2-dichloroethane and this extract is added to the organic phase of the reaction medium. The organic phase is washed with 100 ml of water containing about 0.01 mole of sodium sulfite and the organic phase is then separated. The organic phase is azeotropically distilled to remove any water. The distillation is continued to dryness at atmospheric pressure to leave about 125 grams of crude product with a theoretical yield based on the 0.5 mole of toluene intitially present of about 100 mole percent. Analysis of the crude product by gas-liquid chromatography determines that about 95 weight percent of the crude product consists of mixed isomers of chlorotoluenesulfonyl chloride and about 90 weight percent of the crude product is the 2-chloro-4-toluenesulfonyl chloride isomer.

EXAMPLE 2

A 0.5 mole charge of toluene is brought together with sulfur trioxide in a 1,2-dichloroethane reaction medium in the same manner as in Example 1 except that no diphenylsulfone is present. Analysis by gas-liquid chromatography of a sample quantitatively converted to the sulfonyl chloride derivatives finds the toluene sulfonyl chloride isomers are present in the mole ratios of 91.2:8.6:0.2 for the para-, ortho- and meta-isomers, respectively.

The toluene derivatives in the reaction medium are then monochlorinated, converted to the corresponding sulfonyl chloride and isolated in the manner disclosed in Example 1. The mass of the crude product isolated is about 125 grams, representing a theoretical yield based on the 0.5 mole of toluene present initially of about 100 mole percent. Analysis of the crude product indicates that about 95 weight percent of the crude product consists of mixed isomers of chlorotoluenesulfonyl chloride and about 86 weight percent of the crude product is the 2-chloro-4-toluenesulfonyl chloride isomer.

What is claimed is:

1. In a process for the preparation of 2-chloro-4-toluenesulfonyl chloride by sulfonation of toluene to form toluenesulfonic acid, the nuclear chlorination of toluenesulfonic acid to form chlorotoluenesulfonic acid and the conversion of the chlorotoluenesulfonic acid to the chlorotoluenesulfonyl chloride, the improvement wherein the process comprises the steps of:
   (a) reacting by contacting toluene with sulfur trioxide in an anhydrous, chlorinated hydrocarbon medium to produce in the medium toluenesulfonic acid consisting essentially of the 4-toluenesulfonic acid isomer;
   (b) reacting by contacting the toluenesulfonic acid in the chlorinated hydrocarbon medium from step (a) with gaseous chlorine in the presence of an accelerating amount of an iodine catalyst to produce in the medium chlorotoluenesulfonic acid consisting essentially of the 2-chloro-4-toluene sulfonic acid isomer; and
   (c) reacting by contacting the chlorotoluenesulfonic acid in the chlorinated hydrocarbon medium from step (b) with chlorosulfonic acid to produce in the medium chlorotoluenesulfonyl chloride consisting essentially of the 2-chloro-4-toluenesulfonyl chloride isomer.

2. The improvement as defined in claim 1 wherein the anhydrous, chlorinated hydrocarbon medium is 1,2-dichloroethane and/or dichloromethane.

3. The improvement as defined in claim 1 wherein step (a) is conducted in the presence of an orienting agent selected from the group consisting of diphenylsulfone and ditolylsulfone.

4. The improvement as defined in claim 1 wherein step (a) is conducted at a temperature of from about −10° C. to about 20° C., step (b) is conducted at a temperature of from about 50° C. to about 130° C. and step (c) is conducted at a temperature of from about −20° C. to about 70° C.

* * * * *